(12) United States Patent
Gainor et al.

(10) Patent No.: US 7,377,936 B2
(45) Date of Patent: May 27, 2008

(54) RETRIEVABLE SEPTAL DEFECT CLOSURE DEVICE

(75) Inventors: John Gainor, White Bear Township, MN (US); Jeff Helgerson, Minneapolis, MN (US); Richard S. Kusleika, Eden Prairie, MN (US); Dennis L. Olson, II, White Bear Lake, MN (US)

(73) Assignee: ev3, Inc., Plymouth, MN (US)

( * ) Notice: Subject to any disclaimer, the term of this patent is extended or adjusted under 35 U.S.C. 154(b) by 376 days.

(21) Appl. No.: 10/930,321

(22) Filed: Aug. 31, 2004

(65) Prior Publication Data

US 2005/0033327 A1   Feb. 10, 2005

Related U.S. Application Data

(63) Continuation of application No. 10/093,091, filed on Mar. 6, 2002, now Pat. No. 6,911,037, which is a continuation of application No. PCT/US99/20430, filed on Sep. 7, 1999.

(51) Int. Cl.
*A61F 2/24* (2006.01)

(52) U.S. Cl. .................................... 623/1.11

(58) Field of Classification Search ............... 606/151, 606/213, 215; 623/23.72, 1.15, 1.16, 1.2, 623/1.21, 1.49, 1.51
See application file for complete search history.

(56) References Cited

U.S. PATENT DOCUMENTS

| 2,570,465 | A | 10/1951 | Lundholm |
| 3,123,077 | A | 3/1964 | Alcamo |
| 3,124,136 | A | 3/1964 | Usher |
| 3,166,072 | A | 1/1965 | Sullivan, Jr. |
| 3,646,615 | A | 3/1972 | Ness |
| 3,716,058 | A | 2/1973 | Tanner, Jr. |
| 3,874,388 | A | 4/1975 | King et al. |

(Continued)

FOREIGN PATENT DOCUMENTS

EP    0 362 113 A1    4/1990

(Continued)

OTHER PUBLICATIONS

Ruiz, C.E. et. Al., "The Puncture Technique: A New Method for Transcatheter Closure of Patent Foramen Ovale", Cath. And Cardiovasc. Interv. 53:369-372 (2001).

*Primary Examiner*—Julian W. Woo
*Assistant Examiner*—Christina Getman
(74) *Attorney, Agent, or Firm*—Knobbe Martens Olson & Bear

(57) ABSTRACT

The present invention provides a septal defect closure device (10) having a first occluding disk (30) having a first flexible membrane (32) attached to a first frame (34) and a second occluding disk (20) having a second flexible membrane (22) attached to a separate second frame (24). The first frame has at least two outwardly extending loops joined to one another by flexible joints. These loops are attached to the first membrane to define taut fabric petals when the first disk is in a deployed configuration. A central portion of the first membrane is joined to the central portion of the second membrane via a joining segment, which may comprise a conjoint disk. The flexible joints of the first frame are received within the joining segment. This septal defect closure device provides enhanced retrievability.

31 Claims, 6 Drawing Sheets

U.S. PATENT DOCUMENTS

| | | |
|---|---|---|
| 3,892,232 A | 7/1975 | Neufeld |
| 4,006,747 A | 2/1977 | Kronenthal et al. |
| 4,007,743 A | 2/1977 | Blake |
| 4,060,089 A | 11/1977 | Noiles |
| 4,532,926 A | 8/1985 | O'Holla |
| 4,669,473 A | 6/1987 | Richards et al. |
| 4,688,561 A | 8/1987 | Reese |
| 4,781,177 A | 11/1988 | Lebigot |
| 4,836,204 A | 6/1989 | Landymore et al. |
| 4,873,976 A | 10/1989 | Schreiber |
| 4,884,572 A | 12/1989 | Bays et al. |
| 4,895,148 A | 1/1990 | Bays et al. |
| 4,917,089 A | 4/1990 | Sideris |
| 4,924,865 A | 5/1990 | Bays et al. |
| 4,935,028 A | 6/1990 | Drews |
| 4,976,715 A | 12/1990 | Bays et al. |
| 5,013,316 A | 5/1991 | Goble et al. |
| 5,021,059 A | 6/1991 | Kensey et al. |
| 5,053,047 A | 10/1991 | Yoon |
| 5,059,206 A | 10/1991 | Winters |
| 5,085,661 A | 2/1992 | Moss |
| 5,102,421 A | 4/1992 | Anspach, Jr. |
| 5,108,420 A | 4/1992 | Marks |
| 5,129,906 A | 7/1992 | Ross et al. |
| 5,171,259 A | 12/1992 | Inoue |
| 5,192,301 A | 3/1993 | Kamiya et al. |
| 5,203,864 A | 4/1993 | Phillips |
| 5,236,431 A | 8/1993 | Gogolewski et al. |
| 5,246,441 A | 9/1993 | Ross et al. |
| 5,254,133 A | 10/1993 | Seid |
| 5,258,000 A | 11/1993 | Gianturco |
| 5,261,914 A | 11/1993 | Warren |
| 5,284,488 A | 2/1994 | Sideris |
| 5,334,217 A * | 8/1994 | Das .................. 606/213 |
| 5,342,393 A | 8/1994 | Stack |
| 5,350,399 A | 9/1994 | Erlebacher et al. |
| 5,356,432 A | 10/1994 | Rutkow et al. |
| 5,380,334 A | 1/1995 | Torrie et al. |
| 5,397,331 A | 3/1995 | Himpens et al. |
| 5,400,805 A | 3/1995 | Warren |
| 5,425,744 A * | 6/1995 | Fagan et al. ............ 606/213 |
| 5,433,727 A | 7/1995 | Sideris |
| 5,451,235 A | 9/1995 | Lock et al. |
| 5,470,337 A | 11/1995 | Moss |
| 5,486,193 A | 1/1996 | Bourne et al. |
| 5,505,735 A | 4/1996 | Li |
| 5,507,811 A | 4/1996 | Koike et al. |
| 5,562,704 A | 10/1996 | Tamminmäki et al. |
| 5,578,045 A | 11/1996 | Das |
| 5,601,571 A | 2/1997 | Moss |
| 5,620,461 A | 4/1997 | Muijs Van De Moer et al. |
| 5,634,936 A | 6/1997 | Linden et al. |
| 5,643,317 A | 7/1997 | Pavcnik et al. |
| 5,662,681 A | 9/1997 | Nash et al. |
| 5,702,421 A | 12/1997 | Schneidt |
| 5,709,707 A | 1/1998 | Lock et al. |
| 5,725,552 A | 3/1998 | Kotula et al. |
| 5,728,116 A | 3/1998 | Rosenman |
| 5,733,294 A | 3/1998 | Forber et al. |
| 5,741,297 A | 4/1998 | Simon |
| 5,792,179 A | 8/1998 | Sideris |
| 5,797,960 A | 8/1998 | Stevens et al. |
| 5,810,846 A | 9/1998 | Virnich et al. |
| 5,823,956 A | 10/1998 | Roth et al. |
| 5,827,298 A | 10/1998 | Hart et al. |
| 5,829,447 A | 11/1998 | Stevens et al. |
| 5,843,084 A | 12/1998 | Hart et al. |
| 5,846,261 A | 12/1998 | Kotula et al. |
| 5,853,422 A | 12/1998 | Huebsch et al. |
| 5,855,614 A | 1/1999 | Stevens et al. |
| 5,860,948 A | 1/1999 | Buscemi |
| 5,861,003 A | 1/1999 | Latson et al. |
| 5,879,366 A | 3/1999 | Shaw et al. |
| 5,893,850 A | 4/1999 | Cachia |
| 5,904,703 A | 5/1999 | Gilson |
| 5,919,200 A | 7/1999 | Stambaugh et al. |
| 5,944,738 A | 8/1999 | Amplatz et al. |
| 5,947,997 A | 9/1999 | Pavcnik et al. |
| 5,976,174 A | 11/1999 | Ruiz |
| 5,980,524 A | 11/1999 | Justin et al. |
| 6,024,756 A | 2/2000 | Huebsch et al. |
| 6,059,823 A | 5/2000 | Holman et al. |
| 6,077,281 A | 6/2000 | Das |
| 6,077,291 A | 6/2000 | Das |
| 6,079,414 A | 6/2000 | Roth |
| 6,080,182 A | 6/2000 | Shaw et al. |
| 6,087,552 A | 7/2000 | Gregory |
| 6,096,052 A | 8/2000 | Callister et al. |
| 6,106,532 A | 8/2000 | Koike et al. |
| 6,110,212 A | 8/2000 | Gregory |
| 6,123,715 A | 9/2000 | Amplatz |
| 6,152,144 A | 11/2000 | Lesh et al. |
| 6,156,055 A | 12/2000 | Ravenscroft |
| 6,171,329 B1 | 1/2001 | Shaw et al. |
| 6,174,322 B1 | 1/2001 | Schneidt |
| 6,190,400 B1 | 2/2001 | Van De Moer et al. |
| 6,200,336 B1 | 3/2001 | Pavcnik et al. |
| 6,206,895 B1 | 3/2001 | Levinson |
| 6,206,907 B1 | 3/2001 | Marino et al. |
| 6,210,338 B1 | 4/2001 | Afremov et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,238,416 B1 | 5/2001 | Sideris |
| 6,241,747 B1 | 6/2001 | Ruff |
| 6,245,079 B1 | 6/2001 | Nobles et al. |
| 6,270,515 B1 | 8/2001 | Linden et al. |
| 6,277,140 B2 | 8/2001 | Ginn et al. |
| 6,280,460 B1 | 8/2001 | Bolduc et al. |
| 6,290,674 B1 | 9/2001 | Roue et al. |
| 6,290,702 B1 | 9/2001 | Fucci et al. |
| 6,296,641 B2 | 10/2001 | Burkhead et al. |
| 6,299,597 B1 | 10/2001 | Buscemi et al. |
| 6,306,177 B1 | 10/2001 | Felt et al. |
| 6,312,446 B1 | 11/2001 | Huebsch et al. |
| 6,319,263 B1 | 11/2001 | Levinson |
| 6,319,270 B1 | 11/2001 | Grafton et al. |
| 6,319,276 B1 | 11/2001 | Holman et al. |
| 6,322,563 B1 | 11/2001 | Cummings et al. |
| 6,328,727 B1 | 12/2001 | Frazier et al. |
| 6,334,864 B1 | 1/2002 | Amplatz et al. |
| 6,342,064 B1 | 1/2002 | Koike et al. |
| 6,346,074 B1 | 2/2002 | Roth |
| 6,348,053 B1 | 2/2002 | Cachia |
| 6,355,052 B1 | 3/2002 | Neuss et al. |
| 6,368,339 B1 | 4/2002 | Amplatz |
| 6,379,368 B1 | 4/2002 | Corcoran et al. |
| 6,391,048 B1 | 5/2002 | Ginn et al. |
| 6,419,669 B1 | 7/2002 | Frazier et al. |
| 6,440,152 B1 | 8/2002 | Gainor et al. |
| 6,458,100 B2 | 10/2002 | Roue et al. |
| 6,461,364 B1 | 10/2002 | Ginn et al. |
| 6,468,303 B1 | 10/2002 | Amplatz et al. |
| 6,517,564 B1 | 2/2003 | Grafton et al. |
| 6,537,300 B2 | 3/2003 | Girton |
| 6,551,303 B1 | 4/2003 | Van Tassel et al. |
| 6,551,343 B1 | 4/2003 | Törmälä et al. |
| 6,551,344 B2 | 4/2003 | Thill |
| 6,569,188 B2 | 5/2003 | Grafton et al. |
| 6,596,014 B2 | 7/2003 | Levinson et al. |
| 6,626,917 B1 | 9/2003 | Craig |
| 6,632,238 B2 | 10/2003 | Ginn et al. |
| 6,635,066 B2 | 10/2003 | Tanner et al. |

| | | | | | |
|---|---|---|---|---|---|
| 6,645,225 B1 | 11/2003 | Atkinson | EP | 0 920 842 A1 | 6/1999 |
| 6,719,777 B2 | 4/2004 | Ginn et al. | EP | 0 545 091 B1 | 7/1999 |
| 6,776,784 B2 | 8/2004 | Ginn | EP | 1 046 375 A1 | 10/2000 |
| 6,911,037 B2 | 6/2005 | Gainor et al. | EP | 0 793 457 B1 | 10/2001 |
| 2001/0014800 A1 | 8/2001 | Frazier et al. | EP | 1 214 911 A1 | 6/2002 |
| 2001/0021872 A1 | 9/2001 | Bailey et al. | EP | 1 281 355 A2 | 2/2003 |
| 2001/0023332 A1 | 9/2001 | Hahnen | GB | 2 269 321 A | 2/1994 |
| 2001/0031973 A1 | 10/2001 | Nobles et al. | JP | 3286752 | 12/1991 |
| 2001/0034537 A1 | 10/2001 | Shaw et al. | JP | 7171173 | 7/1995 |
| 2001/0037129 A1 | 11/2001 | Thill | JP | 8141070 | 6/1996 |
| 2001/0039434 A1 | 11/2001 | Frazier et al. | JP | 8196623 | 8/1996 |
| 2001/0039435 A1 | 11/2001 | Roue et al. | WO | WO 85/03857 A1 | 9/1985 |
| 2001/0039436 A1 | 11/2001 | Frazier et al. | WO | WO 90/14796 A1 | 12/1990 |
| 2001/0039450 A1 | 11/2001 | Pavcnik et al. | WO | WO 93/13712 A1 | 7/1993 |
| 2001/0041914 A1 | 11/2001 | Frazier et al. | WO | WO 93/14705 A1 | 8/1993 |
| 2001/0041915 A1 | 11/2001 | Roue et al. | WO | WO 95/28885 | 11/1995 |
| 2001/0049492 A1 | 12/2001 | Frazier et al. | WO | WO 96/32882 | 10/1996 |
| 2002/0055767 A1 | 5/2002 | Forde et al. | WO | WO 97/18762 A1 | 5/1997 |
| 2002/0068950 A1 | 6/2002 | Corcoran et al. | WO | WO 97/41779 A1 | 11/1997 |
| 2002/0169475 A1 | 11/2002 | Gainor et al. | WO | WO 97/42878 A1 | 11/1997 |
| 2002/0183786 A1 | 12/2002 | Girton | WO | WO 98/08462 A2 | 3/1998 |
| 2002/0183787 A1 | 12/2002 | Wahr et al. | WO | WO 98/27868 A1 | 7/1998 |
| 2002/0198563 A1 | 12/2002 | Gainor et al. | WO | WO 99/07289 | 2/1999 |
| 2003/0023262 A1 | 1/2003 | Welch | WO | WO 99/18862 A1 | 4/1999 |
| 2003/0028213 A1 | 2/2003 | Thill et al. | WO | WO 99/18864 A1 | 4/1999 |
| 2003/0045893 A1 | 3/2003 | Ginn | WO | WO 99/18871 A1 | 4/1999 |
| 2003/0050665 A1 | 3/2003 | Ginn | WO | WO 99/40849 A1 | 8/1999 |
| 2003/0055455 A1 | 3/2003 | Yang et al. | WO | WP 99/38454 A2 | 8/1999 |
| 2003/0195530 A1 | 10/2003 | Thill | WO | WO 00/56376 A1 | 9/2000 |
| 2003/0220667 A1 | 11/2003 | van der Burg et al. | WO | WO 00/69365 A2 | 11/2000 |
| 2003/0225421 A1 | 12/2003 | Peavey et al. | WO | WO 01/17435 A1 | 3/2001 |
| 2004/0092973 A1 | 5/2004 | Chanduszko et al. | WO | WO 01/21246 A1 | 3/2001 |
| 2004/0098121 A1 | 5/2004 | Opolski | WO | WO 01/30267 A1 | 5/2001 |
| | | | WO | WO 02/32496 A1 | 4/2002 |
| | FOREIGN PATENT DOCUMENTS | | WO | WO 02/38051 A2 | 5/2002 |
| EP | 0541063 | 5/1993 | WO | WO 02/098298 A1 | 12/2002 |
| EP | 0 474 887 B1 | 6/1994 | WO | WO 03/103476 A2 | 12/2003 |
| EP | 0 655 222 B1 | 6/1998 | | | |
| EP | 0 876 793 A2 | 11/1998 | * cited by examiner | | |

RETRIEVABLE SEPTAL DEFECT CLOSURE DEVICE

CROSS REFERENCE TO RELATED APPLICATIONS

This application is a continuation of U.S. application Ser. No. 10/093,091, filed Mar. 6, 2002, now U.S. Pat. No. 6,911,037 which is a continuation of International Application Number PCT/US99/20430 filed Sep. 7, 1999, which was published in English under PCT Article 21(2), the teachings of which are incorporated herein by reference.

FIELD OF THE INVENTION

The present invention generally relates to minimally invasive devices for occluding a defect and has particular utility in connection with occluding defects in septa, such as atrial septal defects.

BACKGROUND OF THE INVENTION

Considerable efforts have been made to develop remotely deployable occluding devices which can be used to occlude body passageways without requiring significant surgical intervention. A number of researchers have attempted to develop a safe, reliable device which can be deployed through a catheter to occlude a septal defect, such as atrial and ventricular septal defects in the heart. Many of the same devices are used in connection with occluding patent ductus arteriosis (PDA) defects.

One of the first practical systems for reliably occluding septal defects using a transcatheter approach was developed by Dr. Gladwin S. Das and is described in U.S. Pat. Nos. 5,334,217 and 5,578,045 (the teachings of both of which are incorporated herein by reference). All of the devices designed for minimally invasive septal defect occlusion prior to Das' development were cumbersome and relatively difficult to deploy. Most of them were also mechanically complex, greatly increasing the chance of mechanical failure. The simplicity of the Das design greatly facilitated delivery and reduced the likelihood of any mechanical failure of the device.

Briefly, the Das occluder includes a pair of occluding disks attached to one another. In one embodiment illustrated in that patent, each of the disks comprises a membrane with an elastically deformable frame carried about its periphery. The frame is capable of being collapsed so the device may be delivered through a catheter, but is said to be flexible enough to elastically deploy the membrane upon exiting the catheter. The central portions of the two membranes may be attached to one another to define a central "conjoint disk."

In deploying the Das device, the frames of the two disks are collapsed and the device is inserted into the distal end of a delivery catheter. The catheter is passed through the septal defect to be occluded and the first of the two disks is urged out of the catheter for elastic deployment. The second disk is then urged out of the distal end of the catheter on the other side of the defect to position the central conjoint disk within the defect to be occluded.

While the Das device has proven to be a remarkable advance over the state of the art, it has become clear that some further refinements may be advantageous. In particular, the Das device can be a little difficult to retract once deployed. The Das patents discuss a system for holding the occluder on the distal end of the delivery device using a tether. This permits an operator to retain hold of the device in the event of an improper deployment so the device does not float free within the patient's heart or vascular system. Unfortunately, though, it has proven relatively difficult to reliably and safely retract an inappropriately deployed device back into the lumen of the delivery catheter. While it may be possible to retract the right occluding disk (the second disk to exit the catheter) by retaining a grip on the frame of that disk, it can be much more difficult to retract the left disk (the first occluding disk to be deployed) back into the catheter.

A number of other researchers have attempted to provide improved occlusion devices which can be delivered through a transcatheter approach. For example, in U.S. Pat. No. 5,741,297, Simon discloses a device which has a series of arms used to stretch two separate pieces of fabric. In addition to the single wire joining both of the membranes, the membranes are bonded directly to one another, with the bond being spaced well inwardly of the frame. (This relationship is perhaps best seen in FIGS. 2 and 3.) Simon does not discuss in any detail how this device would be retracted if improperly deployed.

Shaw et al. propose a system for manufacturing occlusion devices which are based on some of the same concepts underlying the Das occluder. In particular, in U.S. Pat. No. 5,879,366, Shaw et al. utilize a pair of membranes which are deployed utilizing a wire frame (38 and 54). These two membranes are joined together at an "attachment point 70" which is formed by sintering a relatively small disk 48 of a bonding polymer. As best seen in FIG. 6B, this attachment point is spaced well inwardly of the two frames and represents a relatively small portion of the overall surface area of the occlusion device. This can make it more difficult to center the device within the defect. This also appears to make it more difficult to retract the device back into a catheter once the second disk has been deployed.

SUMMARY OF THE INVENTION

The present invention provides a septal defect closure device which can be used to occlude abnormal body openings, such as septal defects, patent ductus arteriosis or perforations through the wall of a body organ. This device represents an improvement over the Das device in that it can be more readily retracted into a catheter after it has been deployed.

In one particular embodiment, the present invention provides a septal defect closure device which includes a first occluding disk having a first flexible membrane attached to a first frame and a second occluding disk having a second flexible membrane attached to a separate second frame. The first frame has at least two outwardly extending loops joined to one another by flexible joints, with the loops being attached to the first membrane to define taut fabric petals when the first disk is in a deployed configuration. A central portion of the first membrane is attached to a central portion of the second membrane to define a joining segment, which is preferably a conjoint disk. The flexible joints of the first frame are received within the conjoint disk, which greatly simplifies the process of withdrawing the first frame into a catheter for retrieval.

The frame of the second disk may be shaped similarly to the frame of the first disk and have two or more joints received within the conjoint disk. Alternatively, the second frame can be attached to the second membrane entirely outside the conjoint disk.

In a somewhat different embodiment, the invention provides a septal defect closure device having first and second occluding disks, with each disk comprising a flexible, biologically compatible membrane and a frame for elastically deploying the membrane. A central portion of the membrane of the first disk is joined to a central portion of the membrane of the second disk to define a flexible joining segment having a collapsible periphery. Preferably, the frame of the first disk and the frame of the second disk are formed from separate lengths of resilient wire. The frame of the first disk in a deployed configuration defines at least two petals joined to one another via at least two flexible joints, with the petals of the deployed first disk extending outwardly from the joining segment to elastically deploy the first membrane. The flexible joints of the first frame are positioned within the periphery of the joining segment.

In a related embodiment, a septal defect closure device includes a first occluding disk having a first flexible membrane attached to a first frame and a second occluding disk having a second flexible membrane attached to a separate second frame. A central portion of the first membrane is joined to the central portion of the second membrane to define a flexible joining segment having a collapsible periphery. The first frame is attached to the first membrane such that in its deployed configuration it will define at least two petals of taut fabric joined to each other by at least two flexible joints. Again, the flexible joints of the first frame are positioned within the periphery of the joining segment.

DETAILED DESCRIPTION OF THE PREFERRED EMBODIMENTS

Figure 1:
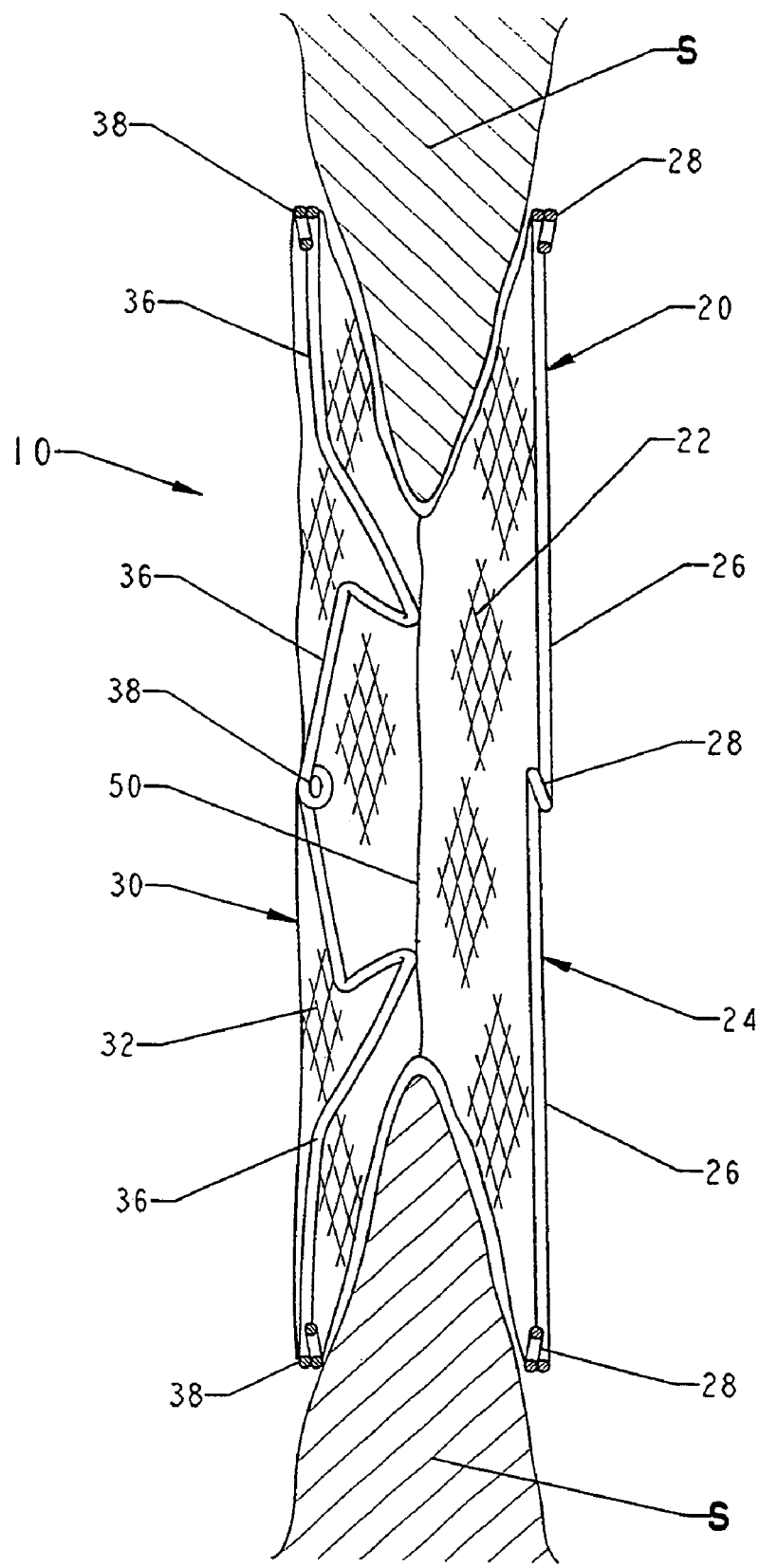
FIG. 1 is a schematic cross sectional side view of one embodiment of a septal defect closure device of the invention.

FIGS. 1-4 illustrate a septal defect occlusion device 10 in accordance with one embodiment of the invention. This septal defect occlusion device includes a proximal occluding disk 20 and a distal occluding disk 30. The proximal occluding disk 20 desirably comprises a flexible, biocompatible membrane 22 and a proximal frame 24. While this proximal occluding disk can take on any desired shape, it is illustrated as being generally square and having the frame 24 extend generally about the periphery of the membrane 22. A variety of other shapes may be selected for this disk 20, depending on the intended application. For example, FIGS. 5A-5F of the Das patents, incorporated by reference above, suggest a series of possible shapes.

The membrane 22 of the proximal occluding disk is preferably formed of a thin, flexible material, such as a fabric which may be folded taut without being damaged. Elastic polymeric materials such as nylon, polyester, polypropylene, polytetrafluoroethylene and expanded polytetrafluoroethylene, as well as natural fabrics such as silk, should meet the requirements of the membrane. In one embodiment which has been found to work well, the membrane 22 is formed of a woven polyester.

The proximal frame 24 is attached to and extends substantially around the periphery of the proximal membrane 22. When the frame 24 is in its natural deployed or non-deformed state, its serves to hold the membrane 22 taut. In the absence of any interference (such as from the septum S in FIG. 1) the frame 24 will tend to pull the membrane 22 into a taut, generally planar shape and the two occluding disks 20, 30 will abut against one another.

Figure 2:
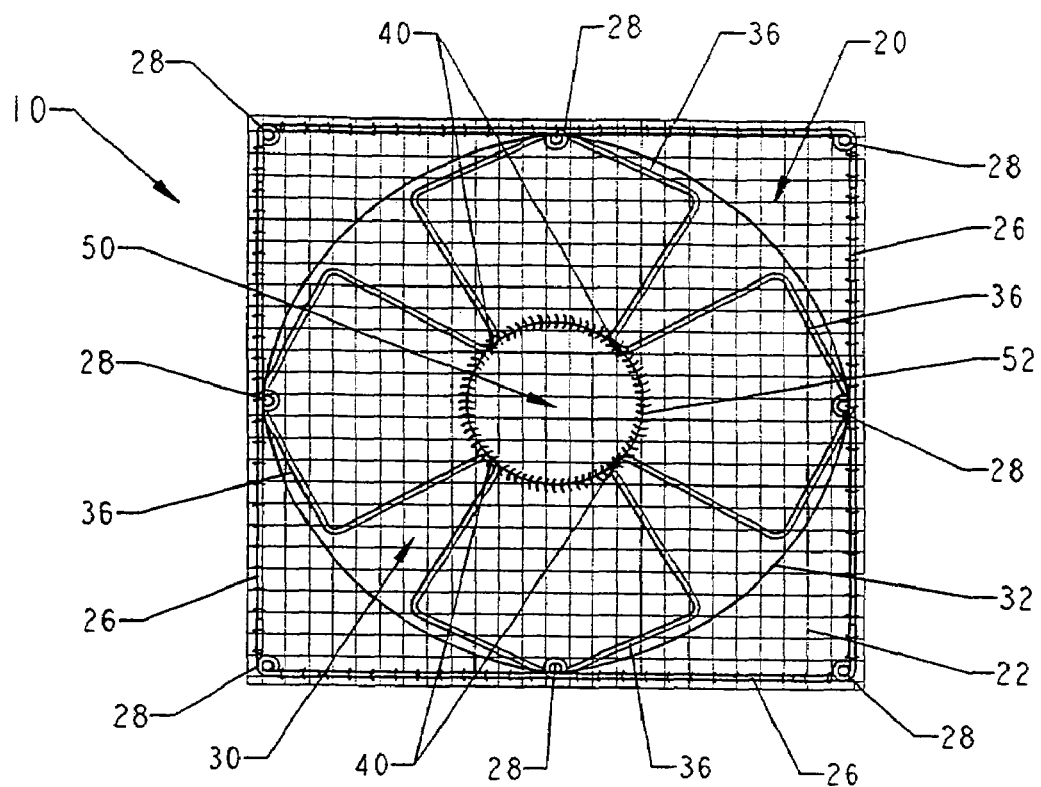
FIG. 2 is a proximal end view of the septal defect closure device of FIG. 1 prior to placement in a patient's body.

The proximal membrane 22 may be attached to the proximal frame 24 by any suitable means. For purposes of illustration, FIG. 2 shows the frame 24 stitched to the fabric membrane 22, with loops of the stitching extending about the wire of the frame. If so desired, though, the membrane may be directly attached to the frame by means of an adhesive. If the membrane 22 is formed of a thermosetting polymeric material (e.g., nylon), the peripheral edge of the membrane may be wrapped around the frame and fused to the body of the membrane by means of heat sealing or the like.

The proximal frame 24 desirably comprises a plurality of elongate legs 26, with each leg being flexibly connected to another leg at each end. Any suitable number of legs may be employed, but the proximal frame 24 of FIGS. 1-3 utilizes 8 legs. Each side of the square frame 24 is defined by a pair of legs 26 generally longitudinally aligned with one another.

The legs 26 of the frame 24 may be connected to one another in any useful fashion. In the illustrated embodiment, the legs 26 are connected to one another by resilient eyelets 28, with one end of the loop-like eyelet attached to each leg. The eyelets 28 may lay in generally the same plane as the legs. These eyelets are desirably formed to function as torsion springs, biasing the legs to which they are attached outwardly into the position illustrated in FIGS. 2 and 3. This helps ensure that the frame will elastically substantially return to its initial configuration even after it has been collapsed and delivered through a catheter, as discussed below in connection with FIGS. 9-11.

Optimally, the proximal frame 24 is formed integrally of a single elongate strand of wire. Each of the legs 26 may simply comprise a length of this wire and the wire may be twisted between adjacent legs to define the eyelets 28. The ends of the wire may be attached to one another in any secure fashion, such as by welding or a suitable biocompatible cementitious material. The frame 24 should be formed of a flexible, elastically deformable material, such as a metal. In a particularly preferred embodiment, the wire comprising the frame is formed of a superelastic material, such as nitinol.

The septal defect occlusion device 10 of FIGS. 1-4 also include a distal occluding disk 30. In the illustrated embodiment, the proximal occluding disk 20 is generally square while the distal occluding disk 30 is generally circular in shape. The distal occluding disk 30 comprises a distal membrane attached to or carried by the distal frame 34. The distal membrane 32 is preferably formed of the same type of material as the proximal membrane. If so desired, one could form each membrane out a different material to achieve a specific design objective.

Whereas the proximal frame 24 extends generally about the periphery of the proximal occluding disk 20, the distal frame 34 takes a more circuitous path. As best seen in FIG. 4, this distal frame 34 comprises 4 equiangularly spaced loops 36 connected to one another by means of flexible joints 40. In particular, each loop 36 is flexibly connected to another loop at each of its ends by such a joint. In the illustrated embodiment, each of these flexible joints comprises a bend in the wire defining the frame. If so desired, eyelets such as those shown at 38 may be included in these flexible joints 40 to further enhance their tendency to restore the device to the natural, non-deformed shape shown in FIG. 3. If so desired, each of the loops 36 may comprise two symmetrical halves, with each half being joined to the other by means of an eyelet 38. These eyelets would serve essentially the same function as the eyelets 28 mentioned above in connection with the proximal occluding disk 20.

Each of the loops 36 of the distal frame 34 should be attached to the distal membrane 32 so that when the loop radially expands into its deployed state, it will pull the membrane relatively taut. Optimally, the membrane is attached to the wire of the frame 34 along most of the frame's length. This can be accomplished, for example, by sewing the fabric membrane to the loops 36. When the loops are fully deployed, they will tend to pull the fabric extending over the loop relatively taut. This will define a petal for each loop. As a consequence, one may view the proximal disk 30 as a series of four equiangularly spaced petals joined to one another by the flexible joints 40 and by the membrane 32. There is some additional fabric extending between the adjacent petals, but the attachment of the membrane to the petals will help pull this interstitial fabric relatively taut even though the frame does not extend around the periphery of these interstitial areas. Pulling these interstitial fabric areas taut against the septum S reduces the chances that blood will freely shunt across the defect between the petals after the device is deployed.

The proximal and distal occluding disks 20, 30 are joined to one another so the device can be readily deployed as a single unit without requiring assembly in situ. In particular, a central portion of the proximal membrane 22 is joined to a central portion of the distal membrane to define a flexible joining segment having a collapsible periphery. In the illustrated embodiment, this joining segment takes the form of a conjoint disk where the two membranes overlap and are directly attached to one another. In the illustrated embodiments, the central portions of the membranes are attached directly to one another to define a conjoint disk 50, but it should be understood that these membranes need not be directly attached to one another or define a conjoint disk to define a suitable joining segment.

The membranes 22, 32 may be affixed to one another by any desired means, such as by using a biocompatible adhesive. The adhesion between the two central membrane portions should be strong enough to ensure that the two disks will not become separated from one another during handling and deployment of the closure device. In the illustrated embodiments, the membranes are sewn to one another, with the stitching defining the shape and size of the conjoint disk. If the membranes are formed of an appropriate polymeric material their central portions may instead be fused by one another by heat sealing or the like. To ensure a better grasp of the flexible joints 40 of the distal frame 34 (as discussed below), however, it is preferred that the disks be sewn together even if they are fused to one another.

If so desired, the membranes 22, 32 may be formed of a thin, highly flexible material and the conjoint disk may include another piece of material (not shown) such as polyurethane or nylon between the two membranes. This extra piece of material may be sewn or otherwise bonded to the membranes to define a more complex conjoint disk. The additional material may be of any size, but it is optimally about the same size as the conjoint disk or slightly larger. This additional piece of material may be coated with a thrombogenic material or the like to more rapidly occlude the defect.

The conjoint disk 50 may be of any desired shape. A general circular shape such as that shown in the drawings has been found suitable. To facilitate relatively quick closure of the defect and to better center the device during deployment in a beating heart, the conjoint disk 50 is desirably sized to substantially fill the defect being occluded, but should not be substantially larger than the defect. Although the size of septal defects tends to vary, most atrial septal defects are smaller than 25 mm in diameter. Accordingly, it is contemplated that a variety of septal defect occluding devices having central conjoint disks 50 ranging in size from about 5 to 30 mm will be provided. A surgeon may measure the size of the defect by known means, e.g., using a balloon catheter filled with a contrast medium, and select a closure device having a conjoint disk of the appropriate size.

It is also desirable that the disks 20, 30 be at least 1.33 times the size of the defect, and preferably range from about 1.33 to 2.5 times the size of the defect. For example, to patch a 10 mm defect, a septal defect occluding device 10 having a central conjoint disk 50 of about 10 mm in diameter and a proximal occluding disk of about 25 mm in maximum dimension may be selected.

As best seen in FIG. 2, the flexible joints 40 of the proximal frame 34 are received within the conjoint disk 50. It is preferred that the flexible joints be attached to the first and second membranes and become a part of the conjoint disk. This can be accomplished in any fashion. For example, if the conjoint disk is made by fusing the two membranes to one another, the portion of the conjoint disk may extend radially beyond each flexible joint such that the two membranes are fused to one another between adjacent loops 36, helping retain the joints 40 within the conjoint disk.

In the illustrated embodiment, though, the stitching which is used to provide the conjoint disk 50 with a collapsible periphery also attaches the frame 34 to the conjoint disk. In particular, at least one stitch covers at least one portion of the distal frame 34 to help retain the flexible joints within the conjoint disk. While the flexible joint could extend farther into the conjoint disk, FIG. 2 illustrates a device wherein one or two stitches covers each of the flexible joints 40 to ensure that they stay in place. As noted above, the flexible joints 40 may include eyelets similar to the eyelets 38 included in the loops 36. If such eyelets (not shown) are used, one may pass at least one stitch through the orifice of at least one of these eyelets (and desirably pass at least one stitch through each such orifice) to hold the eyelets in place.

Figure 4:
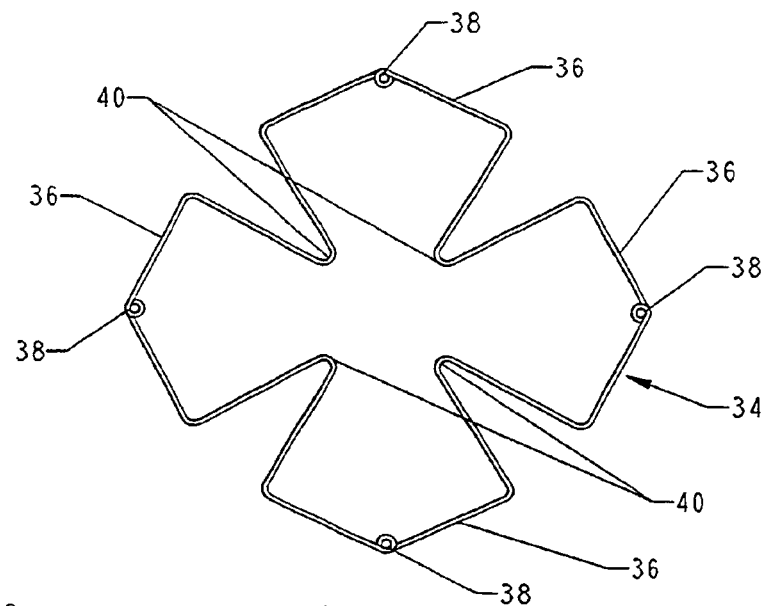
FIG. 4 is a distal end view of the frame of the distal occluding disk of FIGS. 1 and 2.
Figure 5:
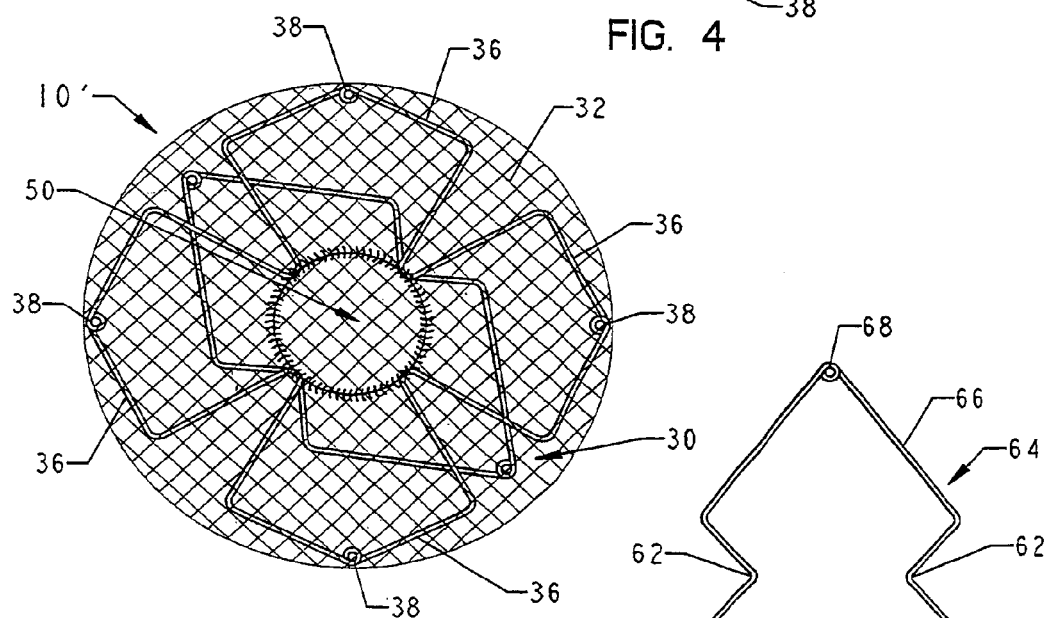
FIG. 5 is a proximal end view of an alternative embodiment of the invention.
Figure 6:
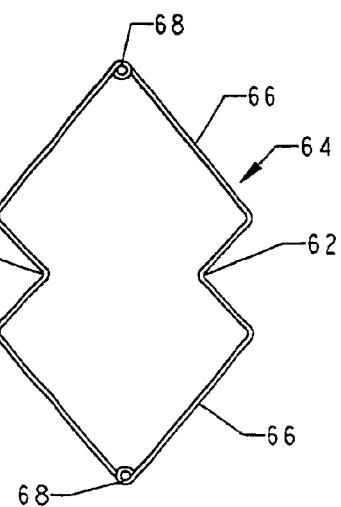
FIG. 6 is an end view of the frame of the proximal occluding disk of the device of FIG. 5.

FIGS. 5 and 6 illustrate an alternative embodiment of the invention. This central defect occluding device 10' also includes proximal and distal occluding disks. The distal occluding disk 30 may be substantially the same as that used in the embodiment of FIGS. 1-4. The proximal occluding disk 60, though, utilizes a notably different frame 64.

Figure 3:
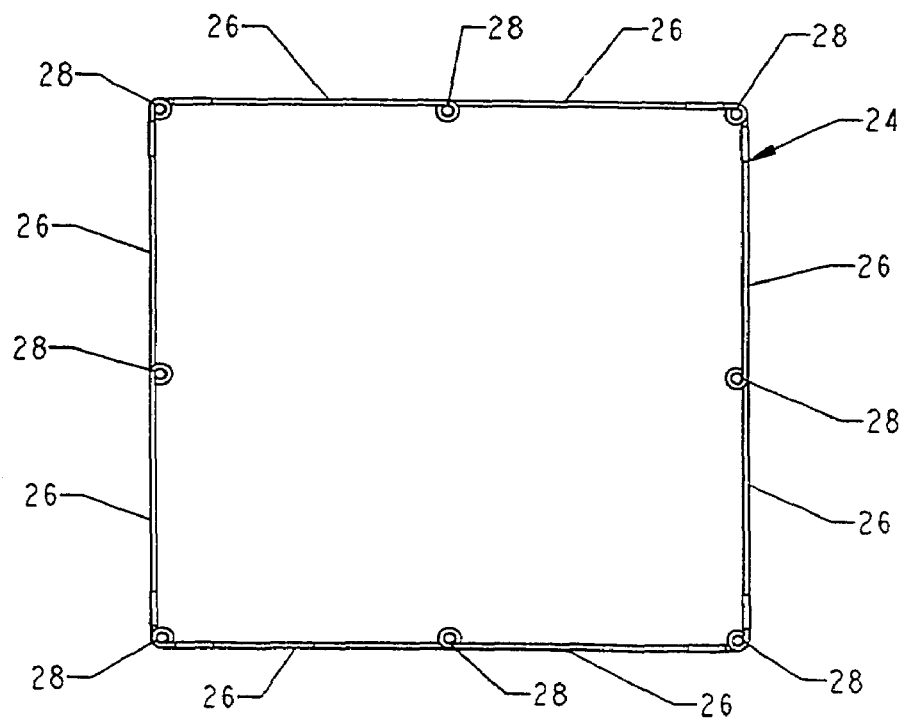
FIG. 3 an end view of the frame of the proximal occluding disk of FIG. 2.

The square proximal frame 24 of FIGS. 1-3 is carried about the periphery of the proximal membrane and is attached to that membrane entirely outside the conjoint disk. The proximal occluding disk 60 of FIG. 5 includes a modified frame 64. The frame 64 includes a pair of generally diametrically opposed loops 66 which extend outwardly from the conjoint disk. The two loops 66 are attached to one another by flexible joints 62, with one joint attaching each end of each loop to an end of the other loop. The loops 66 include spring-type eyelets 68 at their respective apices to further assist in deploying the proximal occluding disk 60. The membrane of the proximal occluding disk 60 may be of any desired shape. If so desired, for example, the membrane may be generally circular in shape and have a diameter which is approximately the same as the maximum dimension of the frame 64 (i.e., the distance between the two eyelets 68). While the efficacy of this approach is still being considered, the membrane may instead take the shape of the frame 64 such that the frame extends about the periphery of the membrane, not unlike the proximal frame 24 of the proximal disk 20 shown in FIGS. 1-4.

Much like the distal frame 34, the flexible joints 62 of the proximal occluding disk 64 are included within the conjoint disk 50. As best seen in FIG. 5, these flexible joints 62 may be positioned immediately adjacent an opposed pair of flexible joints 40 on the frame 34. When the conjoint disk 50 is sewn, stitches used to tie down these opposed flexible joints 40 can also pass over the flexible joints 62 of the proximal occluding disk 60. This will both simplify manufacture and help provide a fairly direct connection between the frame 64 of the proximal occluding disk 60 and the frame 34 of the distal occluding disk 30. As will be explained below, such a connection within the conjoint disk can greatly aid in retracting the device back into a catheter if it is not properly deployed the first time.

Figure 7:
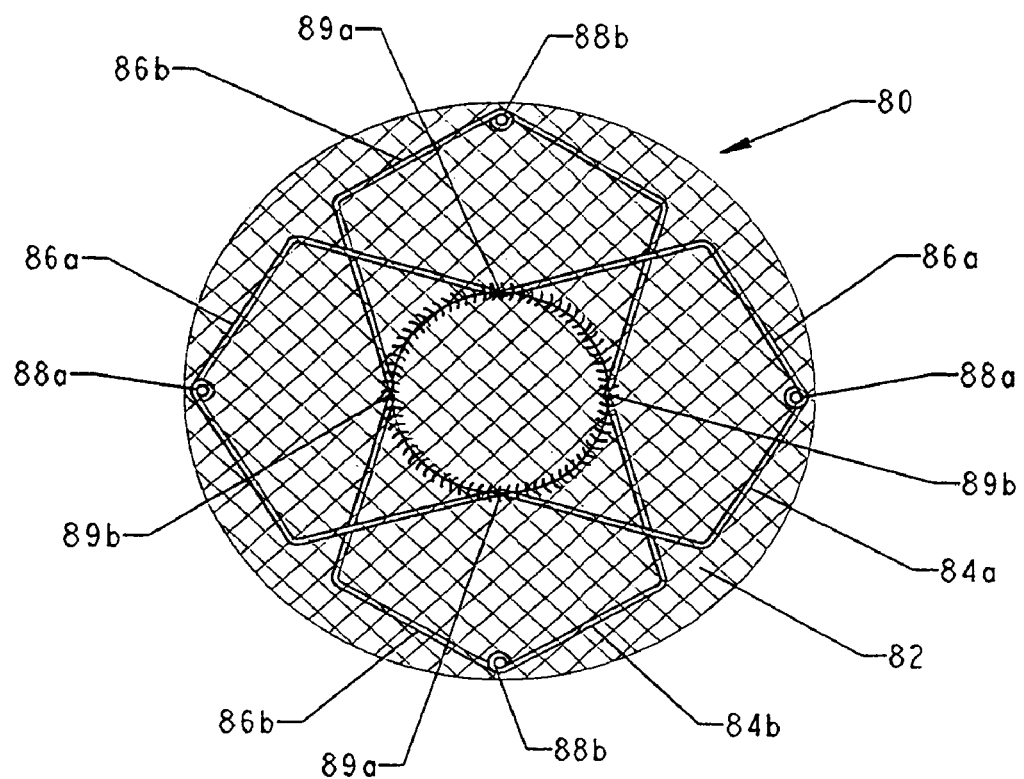
FIG. 7 is an isolation view of a proximal occluding disk in accordance with a preferred embodiment of the invention.
Figure 8:
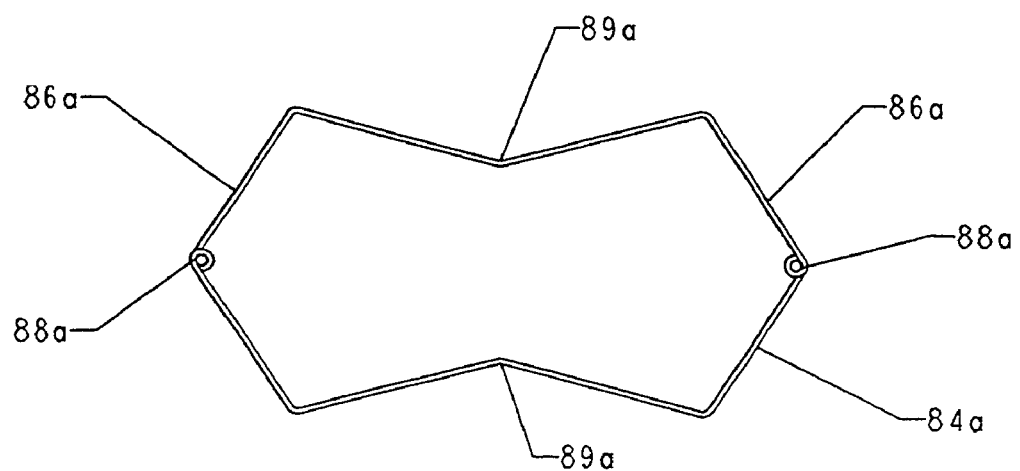
FIG. 8 illustrates one of two frames used in deploying the disk illustrated in FIG. 7.

FIGS. 7 and 8 illustrate an alternative embodiment of a distal occluding disk which may be used in connection with the invention. For purposes of clarity, the proximal occluding disk has been omitted from FIG. 7, but the stitching which would define the conjoint disk of this device has been shown to illustrate how the stitching would attach the frames to the conjoint disk.

The distal occluding disk 80 shown in FIG. 7 has two distal frames 84a and 84b attached to the distal membrane 82. FIG. 8 illustrates one of these two frames, namely frame 84a. This frame includes a pair of diametrically opposed loops 86a joined together by means of flexible joints 89a. If so desired, spring-like eyelets 88a may be provided at the apex of each loop 86a to aid in deployment. Comparison of FIG. 8 to FIG. 6 will highlight the significant structural and functional similarities between the proximal frame 64 shown in FIG. 6 and the distal frames 84a and 84b shown in FIG. 8. The primary difference between these two designs relates to the shape of the loops (66 in FIG. 6 and 86a and 86b in FIG. 8). It should be understood, though, that this difference between the two frames in the drawings is more to illustrate the variety of shapes which can be used to achieve similar function rather than to achieve some significantly different design objective.

The two distal frames 84a and 84b are attached to the membrane 82 such that they are oriented generally perpendicularly to one another. With just two frames, this will ensure that four loops extend generally radially outwardly from the conjoint disk spaced equiangularly on the membrane. The flexible joints 89a and 89b can be stitched to the conjoint disk at 90 degree intervals to enhance the symmetry of the forces acting on the conjoint disk and the force with which the conjoint disk will act on the frames 84a and 84b.

Figure 9:
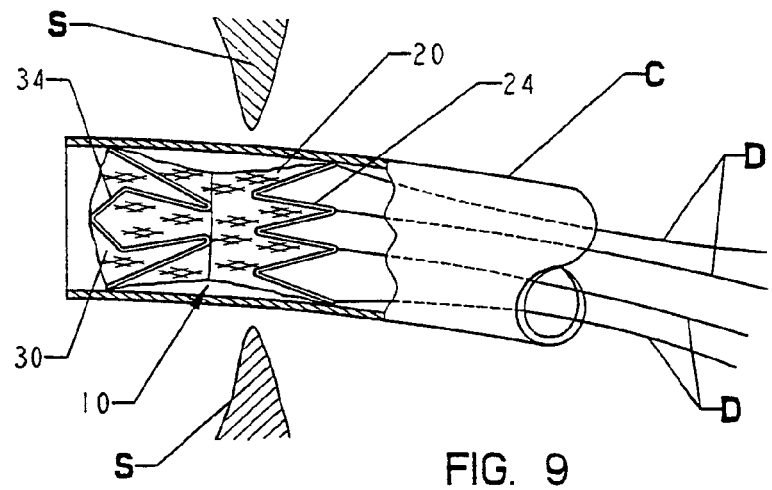
FIGS. 9-11 schematically illustrate deployment of a septal defect closure device in accordance with one embodiment of the invention.
Figure 10:
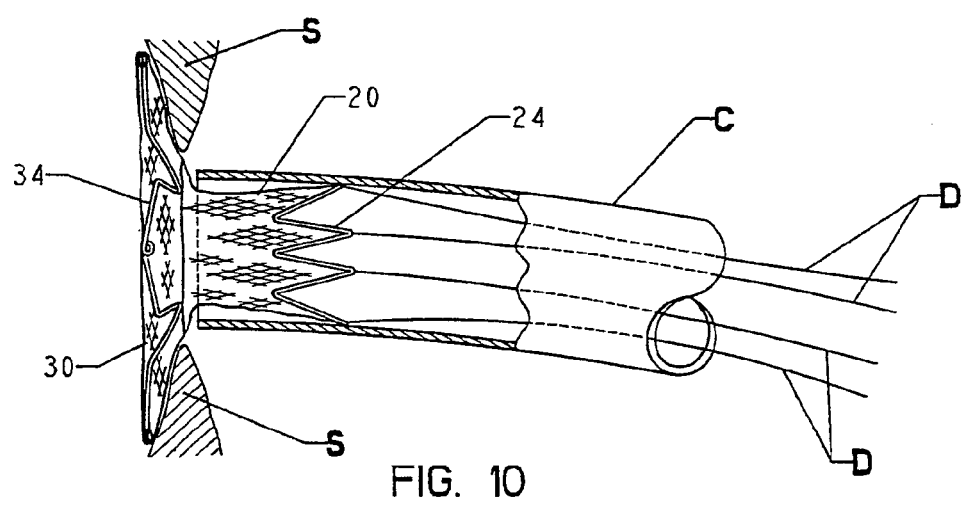
Figure 11:
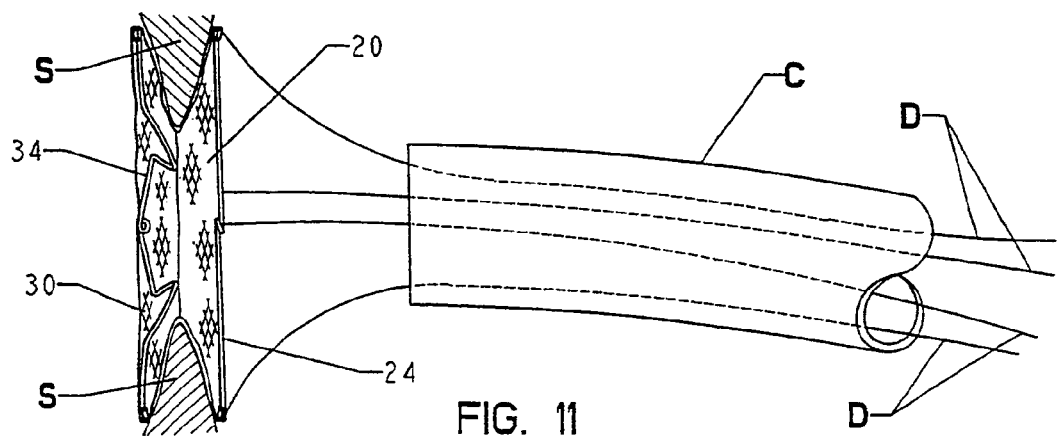

FIGS. 9-11 schematically illustrate the process of deploying the septal defect occluding device 10 of FIGS. 1-4 in a septal defect. Prior to deployment, the occluding device 10 is inserted into the distal end of a catheter C by collapsing the frames 24, 34 of the occluding disks 20, 30. While this can be done manually, it is preferred that the eyelets 28 be used to assist in its insertion. In particular, a pair of drawstrings D may be passed through the eyelets, such as by passing one drawstring through a pair of eyelets in the middle of two opposite sides of the frame and passing the other drawstring through the eyelets in the middle of the other two legs. By pulling these drawstrings D proximally into the catheter C, one can facilitate entry of the first disk into the lumen of the catheter C. Continuing to retract the drawstrings D proximally will collapse the distal occluding disk 30 within the catheter C, as well. Alternatively, the occluding device 10 may be introduced in the proximal end of the catheter and urged distally along the entire length of the catheter until it is near the catheter's distal end.

Before or (more preferably) after insertion of the occluding device 10 into the catheter C, the distal tip of the catheter C is positioned adjacent the defect in the septum S to be occluded. A distal portion of the catheter C should extend through the defect to position the distal tip of the catheter C on the distal side of the defect, as shown in FIG. 9. If the occluding device is introduced into the proximal end of the catheter and advanced to the catheter's distal end, this is preferably done before positioning the catheter so the distal tip of the catheter C will not be inadvertently moved as the device is advanced.

Once the catheter C is properly positioned across the defect, the distal occluding disk 30 is urged out of the distal end of the catheter C. With the constraint of the catheter walls removed, the frame 34 will elastically substantially return to its initial, non-deformed shape (best seen in FIGS. 2 and 4) and pull the membrane taut. The catheter C may then be retracted, retaining the proximal occluding disk 20 within the catheter until the distal occluding disk engages the distal side of the septum S as depicted in FIG. 10. Since the disk is significantly larger than the defect, the frame will engage the septum S. The proximal occluding disk 20 may then be urged out of the distal end of the catheter C on the proximal side of the defect. This may be accomplished by any number of means, such as by urging the disk with a plunger or gingerly retracting the catheter C proximally. Maintaining a light tension on the conjoint disk will both help draw the proximal occluding disk 20 out of the catheter and ensure that it deploys on the proximal side of the defect rather than popping through the defect to deploy on the distal side.

Upon exiting the distal end of the catheter C, the resilient proximal frame 24 will elastically substantially return to its initial, non-deformed shape (FIGS. 2 and 3) and pull the membrane 22 taut. In so doing, the proximal disk 20 will be urged against the proximal wall of the septum S, as shown in FIG. 11. This will also automatically position the conjoint disk 50 within the defect as the conjoint disk serves to connect the distal occluding disk 30, which is disposed on one side of the septum S, to the proximal occluding disk 20, which is disposed on the other side of the septum S. If the physician is satisfied with the location and sizing of the septal defect occlusion device 10, he may withdraw the drawstrings D and retract the catheter, leaving the device in place on the septum S. If two drawstrings are passed through opposed pairs of eyelets 28 in the frame 24, as described above, the drawstrings can be removed simply by releasing one end of each drawstring and pulling the other end of the drawstring proximally to remove the string from the eyelets and thence out of the patient's body.

In many respects, the deployment of this device is fairly similar to the deployment of the DAS device as set forth in U.S. Pat. Nos. 5,334,217 and 5,578,045, incorporated by reference above. One difference between the present invention and the Das device is the ease with which a septal defect occlusion device can be retracted into a catheter after it has been deployed.

Figure 12:
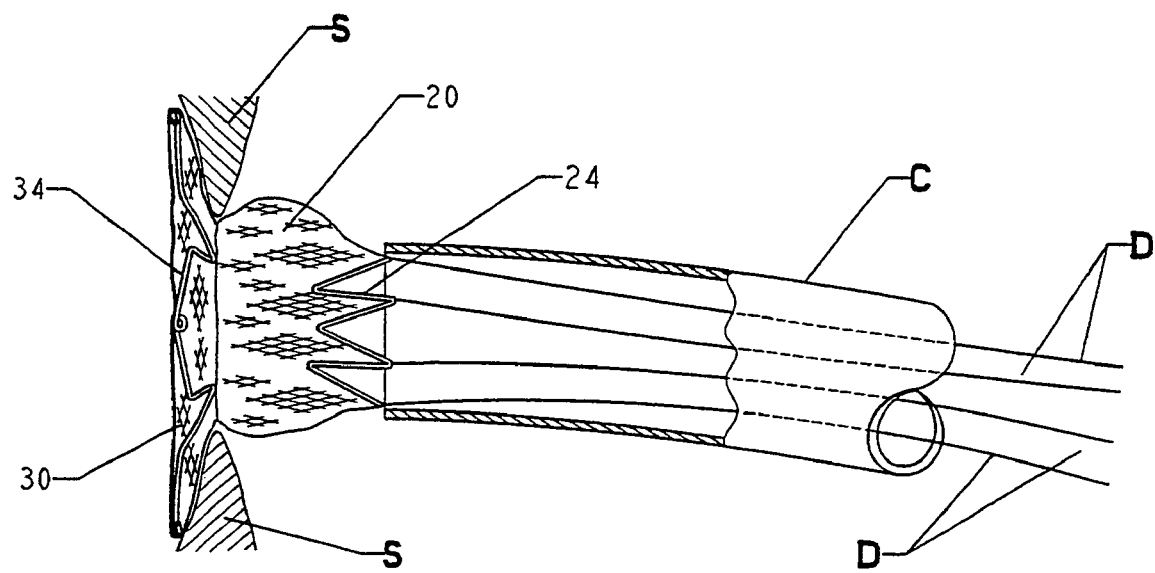
FIGS. 12 and 13 schematically illustrate retraction of the previously deployed septal defect occlusion device shown in FIG. 11.
Figure 13:
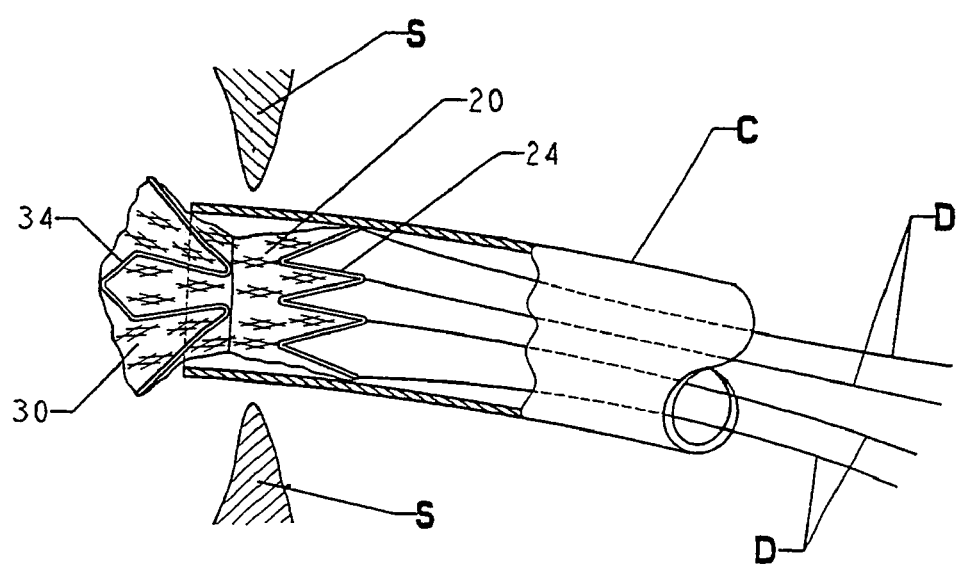

FIGS. 12 and 13 schematically show the deployed septal defect occlusion device of FIG. 11 being retracted into the catheter C. In clinical practice, this can be done for any number of reasons. For example, if a physician selects an inappropriately sized occlusion device, he or she may want to withdraw the deployed device and replace it with a differently sized device. The physician may also want to withdraw a device 10 if it is initially deployed improperly so the same device can be redeployed properly.

In FIG. 12, the proximal occluding disk 20 is being retracted into the distal end of the catheter using the drawstrings D. In so doing, the physician can pull equally on each of the four drawstring ends while advancing the catheter toward the device 10. This will guide the eyelets to which the drawstrings are attached into the end of the catheter. Since the lumen of the catheter is smaller than the deployed frame 24, the catheter walls will collapse the rest of the proximal frame 24 to guide it relatively smoothly into the lumen of the catheter.

In FIG. 13, the catheter C has been advanced distally through the defect so the catheter's distal end is positioned on the distal side of the septum S. This facilitates retracting the distal occluding disk 30 into the catheter without unnecessary trauma to the septum.

In retracting the distal disk into the catheter, the only hold the physician has on the disk 30 is via the conjoint disk 50. In the original Das designs, the frame of both disks is always spaced outwardly from the segment joining the two membranes to one another. As a consequence, as the conjoint disk is being withdrawn into the catheter, it must transmit the force necessary to collapse the frame through the entire fabric of the membrane.

FIGS. 9-11 are simplified schematic illustrations and are not drawn to scale. In most circumstances, the catheter will be much smaller than the conjoint disk, e.g., an occluding device 10 having a conjoint disk 50 with a 10 mm diameter may deployed through a catheter C having a lumen of 3 mm or less in diameter. As a consequence, the flexible conjoint disk and its collapsible periphery will be distorted significantly as it is withdrawn into the catheter. This buckling and folding of the conjoint disk results in an uneven application of force to the membrane. With a peripheral frame such as that used in the Das septal defect closure devices, this makes the collapse of the distal frame relatively difficult and somewhat unpredictable.

The present inventors do not have clinical experience with the devices proposed by Simon in U.S. Pat. No. 5,741,297 or by Shaw et al. in U.S. Pat. No. 5,879,366. However, it appears that these devices would suffer from some of the same disadvantages in retracting the distal part of the device into a catheter or proximally through the septum. In both devices, the connection between the two membranes is relatively narrow and is spaced well away from the wire used to open the membranes against the septum. In the Simon device, this problem may be addressed in a different fashion by using a single wire to form the arms used to deploy both disks—perhaps by retracting this wire, one can draw both membranes into the catheter. The success of such an attempt is far from certain, though.

The attachment point 70 between the two fluoropolymer sheets in the Shaw et al. device is spaced inwardly of the frame (as best seen in FIG. 6B). In this regard, the Shaw et al. device is directly analogous to the Das occluder and is likely to suffer essentially the same difficulties in reliably collapsing the wire on the distal side of the defect back into a catheter in a controlled fashion.

The septal defect occlusion device 10 of the invention addresses these difficulties by positioning the flexible joints 40 of the distal frame 34 within the conjoint disk 50. When the proximal disk is collapsed into the catheter C (FIG. 10) and tension is applied to the drawstrings, the conjoint disk will begin to collapse down into the catheter. Since the joints 40 are retained within (and, in this embodiment, physically stitched to) the conjoint disk, drawing proximally on the conjoint disk pulls more or less directly on more localized, flexible areas of the distal frame 34. This causes the distal frame to begin collapsing at the flexible joints 40. As a consequence, the petals of the distal disk 30 will bend upwardly toward one another (i.e., away from the direction of the septum S), as illustrated in FIG. 13. The distal end of the catheter will act against the loops 36 of the frame 34 to further collapse the petals in a controlled, orderly fashion.

This is a remarkable improvement over the Das device and the expected behavior of the Simon device. In those devices, collapse of the distal disk by the catheter is indirect and not very controlled. In contrast, a septal defect occlusion device of the invention having flexible joints retained within a flexible joining segment attaching the two membranes to one another can be retracted reliably and reproducibly. This enables a physician to fully deploy the device in a septal defect or other abnormal body opening with confidence that he or she can reposition or withdraw the device if its initial deployment is unsatisfactory.

While a preferred embodiment of the present invention has been described, it should be understood that various changes, adaptations and modifications may be made therein without departing from the spirit of the invention and the scope of the appended claims.

What is claimed is:

1. A method of deploying a defect closure device, comprising:
providing an elongate delivery catheter having a lumen;
providing a closure device having expandable proximal and distal frames, the proximal and distal frames being coupled to each other and wherein the distal frame includes a plurality of loops originating from a central attachment region and extending radially outwardly from the central attachment region and including a plurality of flexible joints configured to facilitate collapse of the distal frame upon retrieval, the plurality of flexible joints being disposed on the central attachment region;
reversibly delivering the closure device from the catheter into a defect of a patient such that the proximal and distal frames are fully expanded on opposite sides of the defect and wherein the closure device is capable of being retracted back into the lumen from its fully expanded configuration within the patient by withdrawing a drawstring attached to the proximal frame to collapse the proximal frame and by collapsing the distal frame along the plurality of flexible joints.

2. The method of claim 1, further comprising withdrawing the drawstring for retracting the closure device back into the lumen.

3. The method of claim 1, wherein a distal end of the catheter is advanced distal to the defect before retracting the distal frame of the closure device back into the catheter.

4. The method of claim 3, wherein the distal frame engages the distal end of the catheter for collapsing the distal frame along the plurality of flexible joints.

5. The method of claim 1, further comprising proximal and distal membranes disposed along the proximal and distal frames, the proximal and distal membranes being joined along the central attachment region.

6. The method of claim 5, wherein the central attachment region forms a conjoint disk.

7. The method of claim 1, further comprising a plunger for delivering the closure device from the catheter.

8. The method of claim 1, wherein two drawstrings are attached along a periphery of the proximal frame.

9. The method of claim 8, wherein the two drawstrings are configured to pull radially inward along the periphery of the proximal frame for collapsing the proximal frame.

10. A method of deploying a defect closure device, comprising:
providing an elongate delivery catheter having a lumen;
providing a closure device having expandable proximal and distal frames, at least one frame being covered with fabric, and at least one frame having a plurality of loops originating from a central attachment region and extending radially outwardly from the central attachment region and including a pluralty of flexible joints configured to facilitate collapse of the at least one frame upon retrieval, the plurality of flexible joints being disposed on the central attachment region, wherein each of the plurality of loops extends radially outwardly generally parallel to the plane of the fabric in a fully expanded configuration; and
urging the closure device out from the catheter such that the proximal and distal frames are fully expanded on opposite sides of the defect.

11. A retrievable closure device for sealing a defect in a human heart, comprising:
a proximal occluding disk including a proximal membrane disposed along an expandable proximal frame;
a distal occluding disk comprising an expandable distal frame having a plurality of loops originating from a central attachment region and extending radially outwardly from the central attachment region, the distal frame including a plurality of flexible joints configured to facilitate collapse of the distal occluding disk upon retrieval, the plurality of flexible joints being disposed on the central attachment region; and
at least one drawstring coupled to the proximal occluding disk;
wherein the proximal and distal occluding disks can be fully expanded on opposite sides of the defect and wherein the closure device is retrievable back into a lumen of a delivery catheter by withdrawing the drawstring for collapsing the proximal frame and by collapsing the distal frame along the plurality of flexible joints.

12. The closure device of claim 11, wherein the distal occluding disk includes a distal membrane disposed along the distal frame.

13. The closure device of claim 11, wherein said proximal and distal frames are made of a superelastic material.

14. The closure device of claim 11, wherein two drawstrings are coupled to the proximal occluding disk.

15. The closure device of claim 14, wherein the drawstrings are releasably coupled to locations along a periphery of the proximal frame.

16. The closure device of claim 15, wherein the drawstrings are configured to pull radially inward along the periphery for collapsing the proximal frame.

17. The closure device of claim 15, wherein the drawstrings extend through at least two eyelets disposed along the periphery of the proximal frame.

18. The closure device of claim 17, wherein the eyelets function as torsion springs for facilitating the expansion of the proximal frame at the defect.

19. The closure device of claim 11, wherein the proximal and distal frames are elastically biased into an expanded position.

20. The closure device of claim 11, wherein the proximal and distal occluding disks are configured for independent deployment on opposite sides of the defect.

21. The closure device of claim 11, wherein the proximal and distal occluding disks are each generally round in shape when in an expanded position.

22. The closure device of claim 11, wherein the proximal membrane is formed of a relatively porous material for permitting ingrowth of collagen and fibrous tissue into the material.

23. The closure device of claim 11, further comprising a plunger for urging the closure device out from the delivery catheter during deployment.

24. The method of claim 10, further comprising urging the closure device out from the catheter while the closure device is connected to a string.

25. The method of claim 24, wherein the at least one frame having a plurality of loops is the distal frame, and further comprising retracting the closure device back into the lumen by withdrawing the string attached to the closure device and causing the distal frame to collapse along the plurality of flexible joints positioned within the central attachment region.

26. The method of claim 25, wherein the at least one frame having a plurality of loops comprises eyelets at an apex of each of the loops.

27. The method of claim 26, wherein drawstrings are provided through the eyelets.

28. The closure device of claim 11, wherein each loop has an eyelet positioned at an apex thereof.

29. The closure device of claim 11, wherein the central attachment region is ring-shaped.

30. The closure device of claim 11, wherein the proximal frame comprises a plurality of loops each having an eyelet at an apex thereof.

31. The method of claim 1, further comprising retracting the closure device back into the lumen from its fully expanded configuration within the patient by withdrawing a drawstring attached to the proximal frame to collapse the proximal frame and by collapsing the distal frame along the plurality of flexible joints.

* * * * *

UNITED STATES PATENT AND TRADEMARK OFFICE
CERTIFICATE OF CORRECTION

PATENT NO. : 7,377,936 B2 Page 1 of 1
APPLICATION NO. : 10/930321
DATED : May 27, 2008
INVENTOR(S) : John Gainor et al.

It is certified that error appears in the above-identified patent and that said Letters Patent is hereby corrected as shown below:

On the Cover, Assistant Examiner name, delete "Getman" and insert -- Gettman --, therefore.

On Page 2, Column 11, Line 28, In Claim 10, delete "plurality" and insert -- plurality --, therefore.

On Page 3, Column 11, Line 31, In Claim 10, after "region" delete "," and insert -- ; --, therefore.

On Page 13, Column 9, Line 4, Delete "DAS" and insert -- Das --, therefore.

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

PATENT NO.         : 7,377,936 B2                                        Page 1 of 1
APPLICATION NO.    : 10/930321
DATED              : May 27, 2008
INVENTOR(S)        : John Gainor et al.

It is certified that error appears in the above-identified patent and that said Letters Patent is hereby corrected as shown below:

On the Cover Page, Item (73) Assignee, insert -- Endovascular -- between "ev3" and ", Inc.", therefore.

Signed and Sealed this

Thirty-first Day of March, 2009

JOHN DOLL
*Acting Director of the United States Patent and Trademark Office*